United States Patent [19]
Weinkauf et al.

[11] Patent Number: 5,855,893
[45] Date of Patent: Jan. 5, 1999

[54] *TRICHODESMA LANICUM* SEED EXTRACT AS AN ANTI-IRRITANT IN COMPOSITIONS CONTAINING HYDROXY ACIDS OR RETINOIDS

[75] Inventors: Ronni L. Weinkauf, River Edge; Stephan Samuel Habif, Demarest, both of N.J.; John Brian Bartolone, Bridgeport, Conn.

[73] Assignee: Elizabeth Arden Co., Division of Conopco, Inc., New York, N.Y.

[21] Appl. No.: 986,818

[22] Filed: Dec. 8, 1997

Related U.S. Application Data

[60] Provisional application No. 60/038,008 Feb. 14, 1997.
[51] Int. Cl.$^6$ .............................. A61K 35/78; A61K 7/48
[52] U.S. Cl. ................ 424/195.1; 424/401; 514/557; 514/725; 514/828; 514/844; 514/937; 514/938
[58] Field of Search ................... 424/401, 195.1; 514/828, 844, 937, 938, 557, 725

[56] References Cited

U.S. PATENT DOCUMENTS

| | | | |
|---|---|---|---|
| 3,405,151 | 10/1968 | Pike | 260/410.9 |
| 5,158,975 | 10/1992 | Guichardant et al. | 514/560 |
| 5,252,604 | 10/1993 | Nagy et al. | 514/559 |
| 5,310,556 | 5/1994 | Ziegler | 424/401 |
| 5,362,494 | 11/1994 | Zysman et al. | 424/401 |
| 5,445,822 | 8/1995 | Bracco | 424/401 |
| 5,476,661 | 12/1995 | Pillai et al. | 424/401 |
| 5,516,793 | 5/1996 | Duffy | 514/474 |
| 5,587,149 | 12/1996 | Punto et al. | 424/59 |
| 5,686,405 | 11/1997 | Lebreton et al. | 512/2 |
| 5,690,947 | 11/1997 | Habif et al. | 424/401 |

FOREIGN PATENT DOCUMENTS

| | | |
|---|---|---|
| 173 478 | 3/1986 | European Pat. Off. . |
| 631662 | 1/1995 | European Pat. Off. . |
| 90/07331 | 7/1990 | WIPO . |

OTHER PUBLICATIONS

Ingredient Label 1: A commercial composition containing borage seed oil and retinyl palmitate, (Cheese Brough Ponds, Inc.) 1997.
Derwent Abstract of FR 2704390 dated Nov. 4, 1994.
Derwent Abstract of FR 2604624 dated Apr. 8, 1988.
Derwent Abstract of GB 2271928 dated May 4, 1994.
Medline Abstract of Tollesson et al., "Transepidermal Water Loss and Water Content in the Stratum Corneum in Infantile Sebhorroeic Dermatitis", Acta Derm Venereol (Sweden), Feb. 1993, 73 (1), pp. 18–20.
Medline Abstract of Bahmer et al., "Treatment of Atopic Dermatitis with Borage Seed Oil (Glandol)—A Time Series Analytic Study", Kinderarztl Prax (Germany), Oct. 1992, 60 (7), pp. 199–202.
Coupland et al., "Moderation of Ultraviolet Induced Inflammation In Skin by (n–3) and (n–6) Lipids", Croda Oleochemicals, Oct. 22–25, 1996 (Sydney).
Coupland et al., "New Sources of Lipids Containing Stearidonic Acid–Powerful Moderators of Inflammation", Croda Oleochemicals, Oct. 22–25, 1996 (Sydney).

*Primary Examiner*—Jyothsna Venkat
*Attorney, Agent, or Firm*—Rimma Mitelman

[57] ABSTRACT

Compositions containing hydroxy acids and/or retinoids and further containing *Trichodesma lanicum* seed extract as an anti-irritant/anti-sting agent.

2 Claims, No Drawings

TRICHODESMA LANICUM SEED EXTRACT AS AN ANTI-IRRITANT IN COMPOSITIONS CONTAINING HYDROXY ACIDS OR RETINOIDS

This application claims the benefit of U.S. Provisional application Ser. No. 60/038,008, filed on Feb. 14, 1997 now abandoned.

FIELD OF THE INVENTION

The present invention relates to the use of *Trichodesma lanicum* seed extract in a composition and a method for reducing or eliminating skin irritation or sting induced by hydroxy acids or retinoids.

BACKGROUND OF THE INVENTION

Hydroxy acids (HAs) and retinoids have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g. skin redness and stinging sensation upon application. The irritation can be ameliorated by lowering the amount of an active ingredient in the composition or by reducing the active's penetration through the skin. A serious drawback of both approaches is that the efficacy is impaired. The HA related irritation can be reduced by raising the composition's pH but this method yields reduced efficacy due to a decreased HA penetration through the skin. It is desirable to reduce or eliminate the irritation potential of HAs and/or retinoids while maintaining their efficacy.

European Patent Application 0631722 (Johnson & Johnson) discloses the use of glycolic acid to reduce irritation of the skin by retinol. U.S. Pat. No. 5,252,604 (Nagy et al.) teaches the use of tocopherols for retinoic acid induced irritation. U.S. Pat. No. 5,516,793 (Duffy) discloses the use of ascorbic acid to ameliorate the irritation caused by various topical ingredients, including HAs and retinoids.

U.S. Pat. No. 5,476,661 (Pillai et al.) discloses cosmetic compositions containing 25-hydroxycalciferol and a lipid ingredient. Numerous optional ingredients are listed among which are mentioned HAs and/or retinoids and unsaturated fatty acids, such as gamma linolenic acid (GLA). Pillai et al. do not address the problem of skin irritation, do not teach the use of any agent for reducing skin irritation and do not teach the use of *Trichodesma lanicum* seed extract.

European Patent Application 0416855 (Efamol) discloses treatment of skin damage due to radiotherapy with gamma linolenic acid (GLA) and also teaches a variety of suitable plant sources of GLA, including Borage species. PCT application WO 90/07331 (Went) teaches treatment of inflammation arising from arthritis or headache by topical application of GLA; borage seed is taught as a suitable source. European Patent Application 0173478 (Efamol) discloses treatment of inflammatory skin disorders with compositions containing GLA and glucocorticoids; borage species such as Borago officinalis is mentioned as a rich source of GLA. French patent 2,704,390 (Boiron) discloses an oral supplement containing borage seed oil to provide anti-aging benefits to skin. French patent 2,604,624 (Parfums Rochas) discloses skin care compositions containing polyunsaturated carboxylic acids, such as GLA; borage is said to be rich in GLA. Great Britain Patent 2,271,928 (Laing) discloses the use of borage family plant extracts for alleviation of skin disorders and irritations.

U.S. Pat. No. 5,445,822 (Bracco) discloses cosmetic compositions containing a mixture of polyunsaturated acids' triglycerides, wherein the fatty acids include stearidonic acid. Borage oil is listed as a suitable oil. Role of lipids (triglycerides) in anti-inflammatory processes is described. Tollesson et al., "Transepidermal Water Loss and Water Content in the Stratum Corneum in Infantile Sebhorroeic Dermatitis", Acta Derm Venereol (Sweden), February 1993, 73 (1), p. 18–20, disclose the use of topically applied borage oil for treatment of sebhorroeic dermatitis. Bahmer et al., "Treatment of Atopic Dermatitis with Borage Seed Oil (Glandol)—A Time Series Analytic Study", Kinderarztl Prax (Germany), October 1992, 60 (7), p. 199–202, disclose the use of borage oil for the treatment of atopic dermatitis.

U.S. Pat. No. 5,690,947 (Habif et al.) disclose the use of borage seed oil for alleviating irritation caused by hydroxyl acids or retinoids.

U.S. Pat. No. 5,158,975 (Guichardant et al.) discloses the use of stearidonic acid for inhibiting leukotrienes. The composition may be used topically for treating skin inflammations, e.g. acne, eczema or psoriasis. Coupland et al. disclose in papers presented at IFSCC on 22–25 Oct. 1996 (Sydney) that stearidonic acid is known to possess anti-inflammatory properties and that Crossessential SA 6 (*Trichodesma lanicum*) is a powerful moderator of UV-induced inflammation. Numerous compounds exist, however, that are able to reduce UV-induced irritation, but not hydroxy acid or retinoid-induced irritation (see Example 4).

*Trichodesma lanicum* is a different plant from borage seed oil, albeit both belong to the Boragenous family of plants and *Tricodesma lanicum* is known under a similar English name "wild borage." The Latin names for the two plants differ: *Tricodesma lanicum* for wild borage, and *Borago officinalis* for borage. Although the art teaches the use of borage seed oil, as a source of GLA, *Trichodesma lanicum* or wild borage seed extract is not mentioned. Indeed, *Trichodesma lanicum* seed contains almost 5 times less GLA than borage seed. The unsaturated fatty acid constituency of *Trichodesma lanicum* seed and borage seed is very different:

| CARBON CHAIN | BORAGE % BY WEIGHT | TRICHODESMA LANICUM % BY WEIGHT |
| --- | --- | --- |
| 18:2 n-6 (Linoleic Acid) | 38.8 | 18.7 |
| 18:3 n-6 (γ-Linolenic Acid) | 20.7 | 5.5 |
| 18:3 n-3 (α-Linolenic Acid) | 0.5 | 24.7 |
| 18:4 n-3 (Stearidonic Acid) | 0.1 | 6.5 |

The art discussed above does not teach any compositions containing *Trichodesma lanicum* seed extract in combination with HAs and/or retinoids. The art does not appear to teach the use of *Trichodesma lanicum* seed extract or any of its constituent unsaturated fatty acids to reduce irritation or sting associated with the use of HAs and/or retinoids.

SUMMARY OF THE INVENTION

The present invention includes, in part, a composition containing a cosmetic benefit ingredient selected from the group consisting of hydroxy acids ("HAs") and certain retinoids and further containing *Trichodesma lanicum* seed extract.

The invention also includes a method for reducing irritation or sting induced by the topical application of a composition containing HAs or retinoids, the method comprising topically applying *Trichodesma lanicum* seed extract in an amount effective to reduce irritation induced by the composition. According to the inventive method, *Trichodesma*

*lanicum* seed extract may be co-present with HAs and/or retinoids in the same composition, or *Trichodesma lanicum* seed extract may be applied from a separate composition.

According to the present invention, by virtue of topical application of *Trichodesma lanicum* seed extract, the irritation or sting induced by the topical application of HAs and/or retinoids is reduced or eliminated. It has been found as part of the present invention that not all known anti-irritants, even those that contain GLA or stearidonic acid ameliorate HA/retinoid induced irritation. Furthermore, a compound that alleviates UV-induced erythema does not necessarily control irritation induced by hydroxy acids or retinoids.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition unless otherwise specified.

*Trichodesma lanicum* seed extract is an essential ingredient of the inventive compositions.

*Trichodesma lanicum* seed extract is obtained from the seeds of *Trichodesma lanicum* plant, also known as Wild Borage which is a plant, native to tropical Asia and Australia.

*Trichodesma lanicum* seed extract is employed according to the present invention to reduce or eliminate the skin irritation induced by hydroxy acids and/or retinoids.

The amount of *Trichodesma lanicum* seed extract in the inventive compositions ranges generally from 0.05% to 10% by weight of the composition, preferably from 0.1% to 5%, most preferably from 0.5% to 2%.

Hydroxyacids enhance proliferation and increase ceramide biosynthesis in keratinocytes, increase epidermal thickness, and increase desquamation of normal skin resulting in smoother, younger looking skin.

The hydroxy acid can be chosen from $\alpha$-hydroxy acids, $\beta$-hydroxyacids (e.g. salicylic acid), other hydroxycarboxylic acids (e.g., dihydroxycarboxylic acid, hydroxydicarboxylic, hydroxytricarboxylic) and mixtures thereof or combination of their stereoisomers (DL, D or L).

Preferably the hydroxy acid is chosen from $\alpha$-hydroxy acids having the general structure (1):

(1)

where M is hydrogen or a saturated or an unsaturated, straight or branched hydrocarbon chain containing from 1 to 27 carbon atoms.

Even more preferably the hydroxy acid is chosen from lactic acid, 2-hydroxyoctanoic acid, hydroxylauric acid, glycolic acid, and mixtures thereof. When stereo isomers exist, L-isomer is most preferred.

It is to be understood that depending on the pH of the composition, the hydroxy acid may be present as a salt, e.g. ammonium or potassium or sodium salt.

Although the inventive compositions may have any pH in the general range of 2.5 to 10, the inventive compositions are particularly useful when they are at an acidic pH (especially if they contain a hydroxy acid), most preferably at a pH of 3–4, because such compositions are particularly irritating.

Retinoids enhance keratinocyte proliferation in vitro, increase epidermal thickness and increase collagen synthesis by dermal fibroblasts. This results in protection from sun damage and smoothing of wrinkled skin. The term "retinoids" as used herein includes retinoic acid, retinol, retinal and $C_2$–$C_5$ retinyl esters, because these are the most irritating. Included in the term "retinoic acid" are 13-cis retinoic acid and all-trans retinoic acid.

The term "retinol" includes the following isomers of retinol: all-trans-retinol, 13-cisretinol, 11-cis-retinol, 9-cis-retinol, 3,4-didehydro-retinol. Preferred isomers are all-transretinol, 13-cis-retinol, 3,4-didehydro-retinol, 9-cis-retinol. Most preferred is all-transretinol, due to its wide commercial availability.

Retinyl ester is an ester of retinol. The term "retinol" has been defined above. Retinyl esters suitable for use in the present invention are $C_2$–$C_5$ esters of retinol, preferably $C_2$ and $C_3$ esters, and most preferably $C_2$ ester because it is more commonly available. Retinyl esters included in the invention are also known as: retinyl acetate, retinyl propionate, retinyl butyrate, and retinyl pentanolate.

A particular advantage of the inventive compositions is that higher amounts of hydroxy acids or retinoids may be employed without causing skin irritation. Preferably the amount of the hydroxy acid component present in the composition according to the invention is from 0.01 to 20%, more preferably from 0.1 to 12% and most preferably from 4 to 12% by weight.

A retinoid may be present in the inventive compositions in an amount 33 to 330,000 IU per gram of the composition, preferably 330 to 16,500 IU, most preferably 1,650 to 6,600 IU. Again, a higher amount of a retinoid may be employed in the inventive compositions without causing skin irritation, due to the co-presence of *Trichodesma lanicum* seed extract.

Most preferred inventive compositions containing *Trichodesma lanicum* seed extract anti-irritant include retinol and/or retinyl acetate and/or glycolic acid and/or lactic acid because these ingredients have been found to cause irritation yet they were found to be particularly efficacious at delivering cosmetic benefits.

The skin treatment composition of the invention also includes a cosmetically acceptable vehicle or a carrier which is inert, usually an ingredient present in the highest amounts, and functioning to deliver active or performance ingredients.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition. The amount of vehicle may range from about 2 to about 99 wt %, preferably from about 50 to about 99%, most preferably from about 80 to 99%, by weight of the total composition.

According to the present invention, the vehicle is preferably at least 60 wt. % water, by weight of the vehicle. The inventive compositions are preferably oil-water emulsions, in order to improve dermal delivery of hydroxy acids (See Sah A., "An in-vitro study of the effect of formulation variables and product structure on the delivery of alpha-hydroxy acid (Lactic acid) to skin", MS Thesis, Department of Pharmaceutical Sciences of the College of Pharmacy, University of Cincinnati, Ohio, July 1996). Such improved delivery is frequently accompanied by increased irritation/sting, making the use *Trichodesma lanicum* seed extract in such emulsions particularly critical. In the preferred oil-in-water emulsions according to the present invention, water comprises at least 50 wt. % of the inventive emulsion, most preferably from 50 to 70 wt. %, by weight of the composition.

Optional Skin Benefit Materials and Cosmetic Adjuncts

Various types of active ingredients may be present in cosmetic compositions of the present invention. Actives are defined as skin benefit agents other than emollients and other than ingredients that merely improve the physical characteristics of the composition. Although not limited to this category, general examples include anti-wrinkle compounds and sunscreens and tanning agents.

Sunscreens include those materials commonly employed to block ultraviolet light. Illustrative compounds are titanium dioxide, the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other component materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

According to the present inventive method, the skin irritation induced by the active ingredient is reduced or eliminated by topical application of *Trichodesma lanicum* seed extract. The *Trichodesma lanicum* seed extract may be co-present with the active, or it may be applied to the skin separately from the active.

Product Form and Packaging

The topical skin treatment composition of the invention can be formulated as a lotion, a fluid cream, a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The *Trichodesma lanicum* seed extract may be packaged separately from the composition containing HAs and/or retinoids.

The following specific examples further illustrate the invention, but the invention is not limited thereto. *Trichodesma lanicum* (Wild Borage) seed extract employed in the examples was obtained from Croda Oleochemicals (England) under the tradename Crossessential SA-6.

EXAMPLE 1

Sting Test Method

The objective was to compare the level of stinging and/or burning produced by a test material versus a control after a single application to the cheek/nasolabial fold. Subjects were first screened for their ability to experience a stinging/burning sensation in response to 8% glycolic acid in comparison to base formula. 20 subjects having balanced left/right stinging responses were utilized in the study. Subjects washed the test sites (cheek/nasolabial fold) for thirty seconds with Ivory soap and warm water. The test sites were blotted dry, and the 0.025 mL of test material and control were simultaneously applied by study personnel to the left and right cheek/nasolabial folds. The materials were rubbed into the skin for thirty seconds. Products were applied in a randomized and balanced order across the subject pool. Subjects rated the degree of stinging/burning felt on each side of the face before washing the test sites, immediately after washing the test sites, and during the challenge immediately (time=0) and at 2.5, 5.0, and 7.5 minutes after the study personnel applied the test materials. Subjects recorded the intensity using the following scale:

0—none
1—very slight
2—slight
3—moderate
4—moderately high
5—high
6—extreme

In addition, at the end of the 7.5 minutes, subjects recorded which side of the face experienced more overall discomfort (stinging/burning), and by how much (by: Barely more, Slightly more, Moderately more, or Extremely more).

Statistical Analysis

The parametric paired t-test (two-tailed) was performed to compare the extent of stinging/burning change from baseline (immediately after washing the test sites) at each evaluation time point (0, 2.5, 5.0, and 7.5 minutes) between each treatment comprising a paired comparison test, with subject acting as a block in these analyses. [Ref. *Statistical Methods*, Snedecor and Cochran, Iowa State University Press, 7th Edition, 1980, pp. 84–86]. These results are shown in Table 1 below. In addition, for each subject, the area under the curve was calculated with respect to the change from baseline response profile, one for each of the two treatments comprising a paired comparison test, using the trapezoidal rule. In order to compare the extent of difference in overall stinging/burning response, the difference in areas under the curve between the two treatments for each subject were compared using a parametric paired t-test (two-tailed), with subject acting as a block in these analyses. [Ref. *Statistical Methods*, Snedecor and Cochran, Iowa State University Press, 7th Edition, 1980, pp. 84–86] A p-value of not greater than 0.1 was considered statistically significant. These results are shown in Table 1A below.

In addition, the subject's joint response to the two general questions "Which side of the face has more stinging?", along with "By how much more?", was converted into a single score, then decoded and classified according to treatment perceived to be comparatively more stinging. This gives a directed measure of perceived attribute difference between treatments, based upon the 9 point category directed ordinal difference scale shown below:

| Directed Ordinal Difference Scale | | |
|---|---|---|
| Treatment A More Stinging/Burning Than Treatment B Extreme | Point of No difference | Treatment B More Stinging/Burning Than Treatment A Extreme |
| (−4) (−3) (−2) (−1) (0) | (+1) | (+2) (+3) (+4) |

(0) = No Difference
(+/−1) = Barely More
(+/−2) = Slightly More
(+/−3) = Moderately More
(+/−4) = Extremely More For each paired comparison, these directed differences were compared using the nonparametric Wilcoxon signed rank test, Pratt-*Lehmann version, with subject acting as a block.* [*Ref. Nonparametrics: Statistical Methods Based on Ranks,* by Erich L. Lehmann, Holden-Day, 1975, pp. 130]. These results are shown in Table 1 below.

An emulsion base was prepared having the following formula.

| EMULSION BASE FORMULA | | |
|---|---|---|
| FULL CHEMICAL NAME OR CFTA NAME | TRADE NAME AND % ACTIVE AS RECEIVED | WT. % |
| water, DI | | 46.54 |
| disodium EDTA | Sequesterene Na2 | 0.05 |
| magnesium aluminum silicate | Veegum Ultra | 0.6 |
| methyl paraben | Methyl Paraben | 0.15 |
| simethicone | DC Antifoam Emulsion | 0.01 |
| butylene glycol 1,3 | Butylene Glycol 1,3 | 3.0 |
| hydroxyethylcellulose | Natrosol 250HHR | 0.5 |
| glycerine, USP | Glycerine USP | 2.0 |
| xanthan gum | Keltrol 1000 | 0.2 |
| triethanolamine | Triethanolamine 99 (%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18DEO | 1.5 |
| isostearyl palmitate | Protachem ISP | 6.0 |
| C12–15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | MYRJ 59 | 2.0 |
| sodium stearoyl lactylate | Pationic SSL | 0.5 |
| retinyl palmitate | Vit. A Palmitate 84% | 0.06 |
| hydroxy caprylic acid | Hydroxy caprylic acid | 0.1 |
| water, DI | | q.s. to 99.80 |
| alpha-bisabolol | Alpha-bisabolol | 0.2 |
| pH | | 7–8 |

Additional ingredients in the Examples below were added in place of water. Compositions 1–4 containing ingredients as indicated in Table 1 were tested using the Sting Test Method. The results that were obtained are summarized in Tables 1 and 1A. The higher the mean intensity and area under the curve, the more severe the sensory irritation (stinging/burning).

TABLE 1

Sting Test Results

| COMPOSITION | INGREDIENTS | Mean Intensity at 0 minutes | Mean Intensity at 2.5 min. | Mean Intensity at 5.0 min. | Mean Intensity at 7.5 min. | Overall Discomfort (# of subjects indicating composition was worse) |
|---|---|---|---|---|---|---|
| 1 | Base Formula | 0.05[a] | 0.25[a] | 0.25[a] | 0.35[a] | 0[a] |
| 2 | Control: Base Formula + 8% Giycolic Acid | 1.05 | 1.85 | 2.00 | 2.15 | 20 |
| 2 | Control: Base Formula + 8% Glycolic Acid | 1.35 | 1.75 | 1.95 | 1.65 | 17 |
| 3 | Base Formula + 4% Glycolic Acid | 0.45[a] | 0.60[a] | 0.60[a] | 0.55[a] | 3[a] |
| 2 | Control: Base Formula + 8% Glycolic Acid | 0.86 | 1.14 | 0.90 | 0.86 | 12 |

TABLE 1-continued

Sting Test Results

| COMPOSITION | INGREDIENTS | Mean Intensity at 0 minutes | Mean Intensity at 2.5 min. | Mean Intensity at 5.0 min. | Mean Intensity at 7.5 min. | Overall Discomfort (# of subjects indicating composition was worse) |
|---|---|---|---|---|---|---|
| 4 | Base Formula + 8% Glycolic Acid + 2% *Trichodesma lanicum* Seed Extract | 0.62 | 0.76 | 0.43[a] | 0.33[b] | 8 |

[a]Significantly less stinging/burning than composition #2 ($p < 0.05$)
[b]Significantly less stinging/burning than composition #2 ($p < 0.10$)

TABLE 1A

| Test Material vs. Composition 2 (Base formula + 8% glycolic acid) | % Reduction in Area Under the Curve |
|---|---|
| Composition 1: Base Formula | 87%[a] |
| Composition 3: Base Formula + 4% glycolic acid | 73%[a] |
| Composition 4: Base formula + 8% glycolic acid + 2% *Trichodesma lanicum* Seed Extract | 43%[a] |

[a]Significantly less stinging/burning than composition #2 ($p < 0.05$)

It can be seen from the results in Tables 1 and 1A that the addition of *Trichodesma lanicum* seed extract significantly reduced stinging compared to the composition containing 8% glycolic acid, but no *Trichodesma lanicum* seed extract.

EXAMPLE 2

Subjects were tested according to Irritation Test Method described below.

Irritation Test Method

Four Exposure Patch Test: The objective was to compare the level of irritation produced by various test materials after repeated patch applications. The test materials were held in contact with the skin under occlusive conditions. The outer upper arm of the panelist was designated as the area of application. Bandage type dressing (Scanpor® tape) was used to hold the patches (25 mm Hill Top® Chamber fitted with 18 mm diameter disc of Webril® padding) into place. Both upper arms of the panelist were used. Patches were applied in a balanced random order.

Patches were applied at 9:00 o'clock Monday morning and removed at 9:00 o'clock Tuesday morning (24 hour exposure). A new set of patches was applied at 3:00 o'clock Tuesday afternoon and removed Wednesday morning at 9:00 o'clock (18 hour exposure). A third set of patches was applied at 3:00 o'clock Wednesday afternoon and removed Thursday morning at 9:00 o'clock (18 hour exposure). A final set of patches was applied at 3:00 o'clock Thursday afternoon and removed Friday morning at 9:00 o'clock (18 hour exposure).

Each time the patches were removed, the sites were rinsed with warm water and patted dry. The test sites were then marked with a surgical skin marking pen to ensure location for grading and subsequent patch applications. Test sites were evaluated at 3:00 p.m. on Tuesday, Wednesday, Thursday and Friday of the study, prior to re-patching.

Skin irritation such as moderate redness, dryness, and/or itching of the test site is expected. Swelling of the test sites is possible. If any test has moderate redness or any swelling at evaluation, that particulartest site should not be repatched.

The test sites on each arm were visually ranked by two trained examiners under consistent lighting. The test sites were ranked in order of severity. The examiner ranking responses at the first evaluation period continued ranking the sites each day throughout the study.

In ranking the reactions, the site with the most severe response was given the lowest score. The site with the second most severe response was given the second lowest score, etc. There was no forced ranking. If two or more sites had no response or the same response (no difference between sites), an average of the ranks was assigned. If a site has been discontinued, due to degree of irritation the site retained the rank it received at the time dosing was discontinued.

Statistical Analysis

The ranking results from the patch treatments were statistically compared by nonparametric statistical methods. The test materials containing the anti-irritants were compared to the corresponding control containing only hydroxy acid and/or retinoid, using Friedman's Rank Sum. Treatments were compared to the Formula 2 (control) at each evaluation point using Friedman's analysis with the panelist acting as a block (i.e., each panelist was tested with each test treatment). p-value of<0.1 was considered statistically significant.

Compositions containing ingredients as indicated in Tables 2, 2A and 2B were tested using the Irritation Test Method. 20 subjects were tested for each of Table 2 test and for Table 2A test and 17 subjects were tested for Table 2B test. The results that were obtained are summarized in Tables 2 and 2A. The higher the Sum of Ranks, the less severe the irritation.

TABLE 2

Irritation Test Results

| COMPOSITION | INGREDIENTS | SUM OF RANKS (DAY 4) | % GLA | % SA** |
|---|---|---|---|---|
| 1 | Base Formula | 68.5[a] | 0 | 0 |
| 5 | Control: Base Formula + 8% Glycolic Acid and 0.075% Retinol | 46.5 | 0 | 0 |

TABLE 2-continued

Irritation Test Results

| COMPOSITION | INGREDIENTS | SUM OF RANKS (DAY 4) | % GLA | % SA** |
|---|---|---|---|---|
| 6 | Composition #5 + 3% Black Currant Seed Oil | 58.0 | 0.51 | 0.06–0.12 |
| 7 | Composition #5 + 1% Sambucus | 44.5 | 0 | 0 |

*Significantly less irritating than composition #5.
**SA = stearidonic acid

TABLE 2A

Irritation Test Results

| COMPOSITION | INGREDIENTS | SUM OF RANKS (DAY 3) | SUM OF RANKS (DAY 4) | % SA |
|---|---|---|---|---|
| 1 | Base Formula | 86* | 84* | 0 |
| 2 | Base Formula + 8% Glycolic | 60 | 62 | 0 |
| 8 | Composition #2 + 1% Trichodesma lanicum | 80* | 77 | 0.065 |

*Significantly less irritating than composition #2.

TABLE 2B

Irritation Test Results

| COMPOSITION | INGREDIENTS | Sum of Ranks (DAY 4) | % SA |
|---|---|---|---|
| 9 | Base Formula + 8% glycolic + 0.064% retinol | 27 | 0 |
| 10 | Base Formula + 8% glycolic + 0.076% retinol + 1% Trichodesma lanicum | 24 | 0.065 |

It can be seen from the results in Table 2 that after four exposures, 8% glycolic acid with 0.075% retinol (#5) was significantly more irritating than Base formula #1. 1% Sambucus (#7) or 3% Black Currant Seed Oil (#6) did not significantly reduce the irritation. Sambucus and Black currant seed oil are known anti-irritants. Black currant seed oil also contains 17% GLA and 2–4% stearidonic acid. However, neither agent was effective in reducing alpha hydroxy acid/retinol induced irritation.

By contrast, as demonstrated by the results in Table 2A, Trichodesma lanicum seed extract (composition #8) significantly reduced the irritation induced by Composition #2 (containing 8% glycolic acid), although the composition contained the same amount or even less stearidonic acid than the composition with black currant seed oil. As demonstrated by the results in Table 2B, the addition of Trichodesma lanicum extract to the formula allowed for an addition of ~20% more retinol, with no increase in irritation.

U.S. Pat. No. 5,158,975, (Guichardant et al.) teaches that the anti-inflammatory effect of stearidonic acid is through the inhibition of 5-lipoxygenase and prevention of formation of 5-HETE and LTB4 which play a predominant part in various inflammatory processes of the allergic type (i.e., asthma) of the cutaneous type (i.e., psoriasis and eczema) or of the rheumatic type. Since HA or retinol-induced irritation is not related to these skin disorders or inflammations (acne, eczema, psoriasis), it is surprising that Trichodesma lanicum seed extract reduces HA or retinol-induced irritation.

Furthermore, the effect of Trichodesma lanicum seed extract cannot be attributed to stearidonic acid or GLA, since compounds which contained higher amounts of GLA and the same or even higher amounts of SA were not effective.

COMPARATIVE EXAMPLE 3

Compositions 1, 5 and 11–14 containing ingredients as indicated in Table 3 were tested using the Irritation Test Method described in Example 2. Seventeen subjects were tested. The results that were obtained are summarized in Table 3. The higher the sum of ranks, the less is the irritation.

TABLE 3

Irritation Test Results

| COMPOSITION # | INGREDIENTS | SUM OF RANKS (DAY 4) |
|---|---|---|
| 1 | Base Formula | 74.5[a] |
| 5 | Base Formula + 8% Glycolic + 0.075% Retinol | 61.5 |
| 11 | Composition #5 + 1% Green Tea | 51.0 |
| 12 | Composition #5 + 0.1% K2 Glycyrrohetinic Acid | 54.5 |
| 13 | Composition #5 + 3% Quench T* | 58.5 |
| 14 | Composition #5 + 3% Polyol Prepolymer -2** | 57.0 |

[a]Statistically less irritating than composition #5.
*An anti-irritant from Centerchem (containing water, butylene glycol, kola bean extract, guarana extract, and mate extract).
**An anti-irritant from Penederm, Inc. (CFTA name PPG-12/SMDI).

It can be seen from the results in Table 3 that none of the known anti-irritants tested (none contained GLA or SA) were able to significantly reduce the irritation induced by composition #5 (containing 8% Glycolic acid and 0.075% Retinol).

COMPARATIVE EXAMPLE 4

UV-Induced Erythema Method:

The objective was to determine whether pre-treatment of the skin prior to irradiation with UV light would reduce the level of erythema produced. Twenty two subjects, aged 18 and older, with Fitzpatrick Skin Types I, II, or III were used in the study. MEDs (minimum erythemial dose) (UVA and UVB range, 290–400 nm) were determined for each subject prior to testing using a solar simulator. Test compositions were applied to 4.0 cm$^2$(2.0 cm×2.0 cm) test sites at a dose of 2 mg/cm$^2$ on the lower back using a positive displacement pipet. Test compositions were rubbed into the test sites using gloved fingertips. After 15 minutes, the test sites were irradiated with a single exposure of 1.5 MED of UVA/UVB light using a solar simulator. Erythema was evaluated visually 24 hours after irradiation, by a trained clinical assessor using a 0–4 scale (0=no erythema, 0.5=barely perceptible, faint or diffuse erythema, 1=slight erythema but having uniform response within the area of irradiation, 2=definite erythema, 3=moderate erythema, 4=severe erythema). The non-parametric Wilcoxon signed rank test, Pratt-Lehmann version, was used to compare differences in erythema between test compositions and base compositions, with the subject acting as a block. Test compositions containing ingredients as indicated in Table 4 were tested using this method. The results that were obtained are summarized in Table 4.

| Base Formula A (compositions 17 was used) | |
|---|---|
| INGREDIENT | % W/W |
| Acrylates/$C_{10-30}$ alkyl acrylate crosspolymer 2% solution | 18.00 |
| dimethicone/silivone oils | 6.45 |
| glycerin | 5.00 |
| PPG-15 stearyl ether | 3.00 |
| isocetyl stearate | 2.75 |
| squalene | 2.35 |
| methyl glucose distearate/polyglyceryl stearate | 2.15 |
| butylene glycol | 1.65 |
| diisopropyl dimer dilinoleate | 1.30 |
| pollen extract/soybean and olive and wheat germ oils unsaponifiable | 1.25 |
| steareth-21 | 1.2 |
| amino acid blend | 1.1 |
| polymethyl methacrylate | 1.00 |
| $C_{8-18}$ glycerides | 1.00 |
| sodium PCA | 1.00 |
| hydrolyzed glycosamine glycans/sodium hyaluronate | 0.50 |
| algae extract solution | 0.50 |
| $C_{12-20}$ acid PEG-8 ester | 0.80 |
| triethanolamine 99% | 0.80 |
| sodium hyaluronate 1% sol'n | 0.75 |
| polyacrylamide/$C_{13-14}$ isoparaffin/laureth-7 | 0.50 |
| arachidyl behenate | 0.50 |
| disodium EDTA | 0.10 |
| steareth-2 | 0.30 |
| DL-panthenol | 0.25 |
| methylparaben | 0.20 |
| behenyl alcohol 80 | 0.20 |
| shea butter | 0.20 |
| perfluoropolymethy isopropyl ether | 0.20 |
| propylparaben | 0.10 |
| diazodinyl urea | 0.10 |
| ceramide 6 | 0.02 |
| water | q.s. to 100 |

TABLE 4

Induced Erythema Test Results

| COMPOSITION | INGREDIENTS | ERYTHEMA SCORE |
|---|---|---|
| 17 | Base Formula A | 0.93 |
| 15 | Base Formula A + 5% α-tocopherol | 0.26 |
| 16 | Base Formula A + 5% α-tocopherol + 1.2% green tea polyphenol | 0.29 |

Compositions containing ingredients as indicated in Tables 4A and 4B were tested using the Irritation Test Method described in Example 2, in two separate experiments. Twenty two subjects were tested for experiment in Table 4A and nineteen subjects for experiment in Table 4B. The results that were obtained are summarized in Tables 4A and 4B.

TABLE 4A

Irritation Test Results

| COMPOSITION # | INGREDIENTS | SUM OF RANKS (DAY 4) |
|---|---|---|
| 1 | Base Formula | 102* |
| 2 | Base Formula + 8% Glycolic | 67 |
| 18 | Composition #2 + 5% α-tocopherol | 64.5 |

*Significantly less irritating than composition #2.

TABLE 4B

Irritation Test Results

| COMPOSITION # | INGREDIENTS | SUM OF RANKS (DAY 4) |
|---|---|---|
| 2 | Base Formula + 8% Glycolic | 72.5 |
| 18 | Composition #2 + 5% α-tocopherol | 77.5 |
| 19 | Composition #2 + 5% α-tocopherol + 1.2% Green tea polyphenols | 56.5 |

As shown in Table 4, when a-tocopherol and green tea polyphenol are added to Base Formula A (composition 17) significant reduction in UV-induced erythema was achieved. However, the results in Tables 4A and 4B show that a-tocopherol and green tea polyphenols were not effective in reducing HA induced irritation.

In CRODA product literature "Moderation of ultraviolet induced inflammation in skin by (n–3) and (n–6) lipids" Coupland et al. report the use of *Trichodesma lanicum* extract (Trichodesma; Crossential SA6) as an inhibitor of PGE2 release that is induced by UVB light. However, it is not obvious that materials which inhibit UV-induced PGE2 production and subsequent irritation, would be effective in reducing HA or retinoid induced irritation, since several materials which inhibit UV induced erythema (such as α-tocopherol and green tea polyphenols) are not effective in reducing HA-induced erythema.

EXAMPLE 5

A typical oil-in-water emulsion within the scope of the invention is as follows:

| chemical name | wt. % |
|---|---|
| propylene glycol | 1 |
| glycerin | 1 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| dimethicone | 0.5 |
| cholesterol | 0.5 |
| cetyl alcohol | 0.5 |
| isostearic acid | 3 |
| retinyl palmitate | 0.1 |
| peg-40 stearate | 1 |
| peg-100 stearate | 1 |
| sorbitan stearate | 1 |
| *Trichodesma lanicum* seed extract | 0.5 |
| glycolic acid | 7 |
| ammonium hydroxide | to pH 4.0 |
| water DI | qs to 100% |

EXAMPLE 6

Another typical oil-in-water emulsion within the scope of the invention is as follows:

| chemical name | wt. % |
|---|---|
| propylene glycol | 1 |
| hydroxyethylcellulose | 0.5 |
| magnesium aluminum silicate | 0.5 |

-continued

| chemical name | wt. % |
|---|---|
| imidazolidinyl urea | 0.2 |
| petrolatum | 2 |
| isopropyl palmitate | 5 |
| dimethicone | 0.5 |
| cholesterol | 0.5 |
| stearic acid | 3 |
| isostearic acid | 1.5 |
| glycerol stearate | 1.5 |
| peg-40 stearate | 1 |
| peg-100 stearate | 1 |
| sorbitan stearate | 1 |
| cetyl alcohol | 0.5 |
| *Trichodesma lanicum* seed extract | 2 |
| glycolic acid | 10 |
| ammonium hydroxide | to pH 3.8 |
| water DI | qs to 100% |

EXAMPLE 7

A typical water-in-oil dispersion within the scope of the invention is as follows:

| chemical name | wt. % |
|---|---|
| isostearyl neopentanoate | 20 |
| peg-8 caprylic/capric glycerides | 6 |
| cetyl octanoate | 17 |
| polyglyceryl-6 dioleate | 15 |
| cyclomethicone | 20 |
| glyceryl isostearate | 0.5 |
| isostearic acid | 0.5 |
| ceramide III | 0.1 |
| ppg-5-cetheth-20 | 3 |
| L-lactic acid/potassium lactate | 6 |
| hydroxycaprylic acid | 0.1 |
| water DI | 1.3 |
| *Trichodesma lanicum* seed extract | 0.5 |

EXAMPLE 8

The following oil-in-water emulsion within the scope of the invention is prepared:

| chemical name | wt. % |
|---|---|
| glycerin | 1 |
| tetrasodium EDTA | 0.1 |
| cetyl alcohol | 1 |
| stearyl alcohol | 1 |
| mineral oil | 5 |
| dimethicone | 1 |
| cyclomethicone | 0.5 |
| dimethiconol | 0.2 |
| polyquaternium-37 | 2 |
| steareth-21 | 1 |
| steareth-2 | 0.5 |
| salicylic acid | 2 |
| *Trichodesma lanicum* seed extract | 0.5 |
| triethanolamine to pH | 3.0 |
| water DI | qs to 100% |

EXAMPLE 9

The following oil-in-water emulsion within the scope of the invention is prepared:

| chemical name | wt. % |
|---|---|
| xanthan gum | 0.2 |
| disodium EDTA | 0.1 |
| sodium PCA | 0.5 |
| diazodinyl urea | 0.3 |
| titanium dioxide | 1 |
| stearic acid | 3 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| *Trichodesma lanicum* seed extract | 0.5 |
| glycolic acid | 3 |
| malic acid | 2 |
| lactic acid | 2 |
| green tea extract | 1 |
| triethanolamine | to pH 3.8 |
| water DI | qs to 100% |

EXAMPLE 10

The following oil-in-water emulsion within the scope of the invention is prepared:

| chemical name | wt. % |
|---|---|
| all-trans retinoic acid | 0.05 |
| light mineral oil | 10 |
| stearoxytrimethylsilane and stearyl alcohol | 5 |
| dimethicone | 2 |
| stearyl stearate | 10 |
| quaternium-15 | 3 |
| peg-22 dodecyl glycol copolymer | 1 |
| *Trichodesma lanicum* seed extract | 1 |
| sorbitol | 0.5 |
| methyl paraben | 0.2 |
| disodium EDTA | 0.1 |
| butylated hydroxytoluene | 0.1 |
| water DI | qs to 100% |

EXAMPLE 11

The following oil-in-water emulsion within the scope of the invention is prepared:

| chemical name | wt. % |
|---|---|
| squalane | 20 |
| macadamia oil | 5 |
| pentaerythritol tetraoctanoate | 15 |
| petrolatum | 5 |
| glyceryl stearate | 3 |
| tocopherol acetate | 0.5 |
| butylated hydroxytoluene | 0.05 |
| methyl paraben | 0.15 |
| propyl paraben | 0.15 |
| retinol | 0.1 |
| *Trichodesma lanicum* seed extract | 0.25 |
| sodium citrate | 1 |
| ascorbic acid | 1 |
| butylene glycol | 2 |
| glycerol | 2 |
| bentone clay | 0.2 |
| disodium EDTA | 0.05 |
| water DI | qs to 100% |

EXAMPLE 12

The following oil-in-water emulsion within the scope of the invention is prepared:

| INGREDIENT | WEIGHT PERCENT |
|---|---|
| Water | 63.15 |
| Cyclomethicone | 7.00 |
| Octyl Methoxycinnamate | 6.00 |
| Isononyl Isononanoate | 4.50 |
| Oxybenzone | 3.00 |
| Glycerin | 3.00 |
| Tridecyl Salicylate | 2.00 |
| Isostearic Acid | 1.20 |
| Steareth-21 | 1.20 |
| Glyceryl Stearate | 1.02 |
| Aluminum Starch Octenylsuccinate | 1.00 |
| Octyldodecyl Neopentanoate | 1.00 |
| Cetyl Alcohol | 0.80 |
| PEG-100 Stearate | 0.68 |
| *Trichodesma lanicum* Seed Extract | 0.50 |
| Panthenol | 0.50 |
| Ethylene/VA Copolymer | 0.40 |
| Triethanolamine | 0.35 |
| Sodium Lactate | 0.30 |
| Steareth-2 | 0.30 |
| Ascorbyl Tetraisopalmitate | 0.20 |
| $C_{12-20}$ Acids PEG-8 Ester | 0.20 |
| Dimethicone | 0.20 |
| Sclerotium Gum | 0.20 |
| Trilaureth-4 Phosphate | 0.20 |
| DMDM Hydantoin | 0.17 |
| Acrylates/C10–30 Alkyl Acrylates Crosspolymer | 0.17 |
| Methylparaben | 0.158 |
| Disodium EDTA | 0.10 |
| Fragrance | 0.10 |
| Propylparaben | 0.10 |
| Tocopherol | 0.10 |
| Algae Extract | 0.085 |
| Propylene Glycol | 0.080 |
| Sage (Salvia Officinalis) Extract | 0.040 |
| Retinyl Linoleate | 0.010 |
| Sodium Hyaturonate | 0.002 |
| TOTAL | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A composition comprising:

(i) a cosmetic benefit ingredient selected from the group consisting of glycolic acid, lactic acid and mixtures thereof in an amount from about 0.1 to about 12% by weight of the composition and retinol in an amount from 330 to 16,500 IU per gram of the composition and mixtures thereof;

(ii) *Trichodesma lanicum* seed extract in an amount from about 0.05% to about 10% by weight of the composition; and (iii) a cosmetically acceptable vehicle.

2. A method for reducing sting or irritation induced by the topical application of a composition containing glycolic acid, lactic acid and mixtures thereof, or retinol, the method comprising topically applying a composition comprising:

(i) a cosmetic benefit ingredient selected from the group consisting of glycolic acid, lactic acid and mixtures thereof in an amount from about 0.1 to about 12% by weight of the composition and retinol in an amount from 330 to 16,500 IU per gram of the composition and mixtures thereof;

(ii) *Trichodesma lanicum* seed extract in an amount from about 0.05% to about 10% by weight of the composition; and (iii) a cosmetically acceptable vehicle.

* * * * *